US00PP35646P2

(12) United States Plant Patent
Hansen

(10) Patent No.: US PP35,646 P2
(45) Date of Patent: Feb. 6, 2024

(54) ***BERGENIA* PLANT NAMED 'PEPPERMINT PATTY'**

(50) Latin Name: ***Bergenia* hybrid**
Varietal Denomination: Peppermint Patty

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 18/445,328

(22) Filed: Jul. 11, 2023

(51) Int. Cl.
*A01H 5/02* (2018.01)
*A01H 6/80* (2018.01)

(52) U.S. Cl.
USPC ..... Plt./409

(58) Field of Classification Search
USPC ..... Plt./409
See application file for complete search history.

*Primary Examiner* — Susan McCormick Ewoldt

(57) ABSTRACT

A new and distinct Heartleaf *Bergenia* plant, *Bergenia* plant named 'Peppermint Patty' with a dense mounded habit, medium to large-sized, densely-arranged, deep-green, glossy, obovate, evergreen foliage with serrate to dentate and ciliolate margins. The flowers are campanulate on large heavily-branched panicles over a long period beginning in spring. The flowers open white and develop pink centers and margins and hold up well in the garden as a landscape plant or as cut flowers. The new plant has a medium growth rate and the foliage is naturally resistant to deer and rabbit foraging.

1 Drawing Sheet

Botanical designation: *Bergenia* hybrid.
Cultivar denomination: 'Peppermint Patty'.

STATEMENT REGARDING PRIOR DISCLOSURES UNDER 37 CFR 1.77(b)(6)

The first non-enabling disclosure of the claimed plant was Dec. 1, 2022, when the claimed plant was displayed as a photograph with a non-enabling brief description on a website maintained by Walters Gardens, Inc. The first plants of *Bergenia* 'Peppermint Patty' offered for sale were by Walters Gardens, Inc. on Jul. 12, 2022. Walters Gardens, Inc. obtained the new plant and all information about the new plant directly from the inventor. No other plants have been sold earlier than this date anywhere in the world, nor has any disclosure of the new plant been made more than one year prior the filing date of this application, and such disclosure within one year was either derived directly or indirectly from the inventor.

BACKGROUND OF THE PLANT

The present invention relates to the new and distinct Heartleaf *Bergenia* herein also referred to as *Bergenia* 'Peppermint Patty', by the cultivar name, 'Peppermint Patty', or as the new plant. The new plant was hybridized by the inventor on Mar. 14, 2014, from a cross-pollination plant of *Bergenia* 'Sakura' (not patented) as the female or seed parent and the proprietary unreleased unnamed hybrid known only as 12-1-6 (not patented) as the male or pollen parent. The cross was performed in a greenhouse of a wholesale perennial grower in Zeeland, Michigan. The single seedling represented by 'Peppermint Patty' was selected from a group of seedlings by the inventor, isolated, compared in subsequent years to other *Bergenia* and subsequently found to be different from all cultivars known to the discoverer, and given the breeder code 14-13-111 through the remaining evaluation process.

Asexual propagation at the same nursery in Zeeland, MI, USA initially by basal cuttings and later by shoot tip sterile tissue culture has shown 'Peppermint Patty' to be stable and reproduce true to type in successive generations since late summer of 2016.

SUMMARY OF THE PLANT

*Bergenia* 'Peppermint Patty' has not been observed in all possible environmental conditions. The phenotype may vary slightly with changes in environments such as light intensity, fertility, water availability, etc. without any variations in genotype.

*Bergenia* 'Peppermint Patty' is distinct from all cultivars known to the inventor in the following traits:

1. Dense mounded habit;
2. Medium to large-sized, densely-arranged, deep-green, glossy, obovate, evergreen foliage with ciliolate margins;
3. Heavily-branched, large panicles of large campanulate flowers over a long period in spring;
4. Flowers open white and develop pink centers and margins;
5. Medium growth rate;
6. Foliage is naturally resistant to deer and rabbits.

Plants of *Bergenia* 'Peppermint Patty' are most similar to: 'Apple Blossom' U.S. Plant Pat. No. 15,101, 'Flirt' U.S. Plant Pat. No. 26,355, 'Miss Piggy' U.S. Plant Pat. No. 32,132, 'Fairytale Romance' U.S. Plant patent application Ser. No. 17/803,929, and 'Spring Fling' U.S. Plant Pat. 26,337.

'Apple Blossom' has a slightly smaller habit with flowers that are a light pink, and the leaf margins that are not ciliolate. 'Miss Piggy' has a slightly smaller habit and deeper pink flowers, and the foliage does not have ciliolate margins. 'Fairytale Romance' has a smaller habit, the flowers are smaller and more solid light-pink, and the foliage is smaller without ciliolate margins. 'Spring Fling' has a shorter habit and denser panicles of deeper pink flowers.

The female parent, 'Sakura', has a smaller habit with shorter, smaller peduncles, deeper pink flowers, and foliage that is smaller and without ciliolate margins. The male parent has smaller white flowers at least one week earlier, and the foliage is more deciduous with a more ciliolate margin.

BRIEF DESCRIPTION OF THE DRAWINGS

The color drawings illustrate the overall characteristics of *Bergenia* 'Peppermint Patty' as a three-year-old plant. The colors are as true as reasonably possible given the technology available. The color values may vary slightly depending on light intensity and quality.

DETAILED BOTANICAL DESCRIPTION

Figure 1:
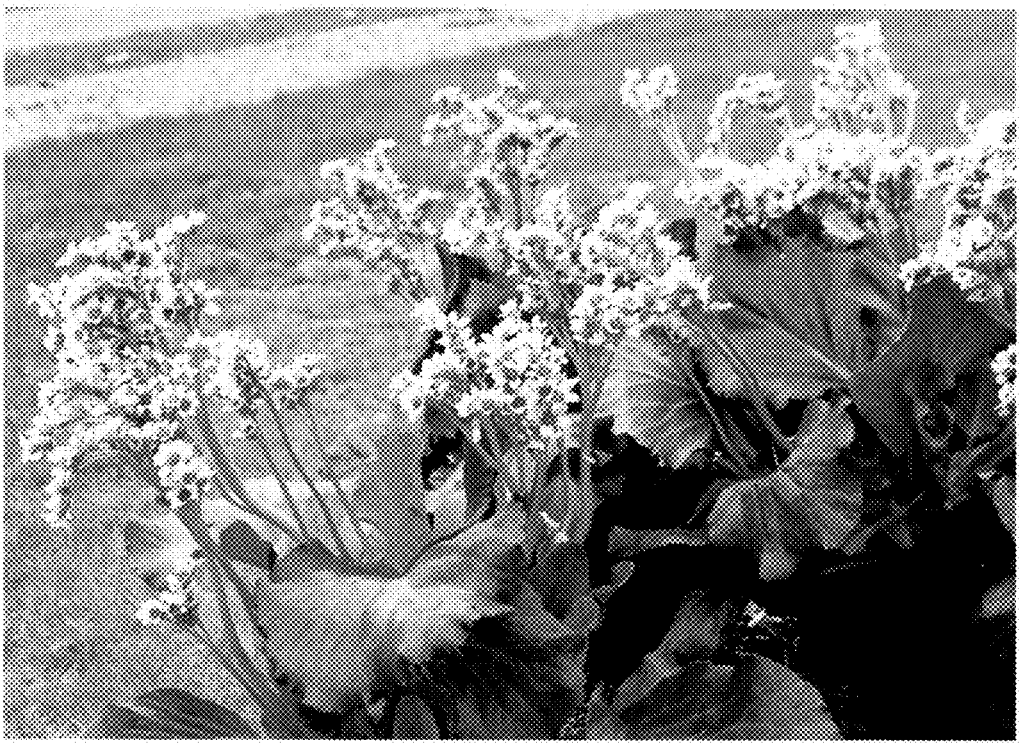
FIG. 1 shows the new plant in a full-sun landscape environment.
Figure 2:
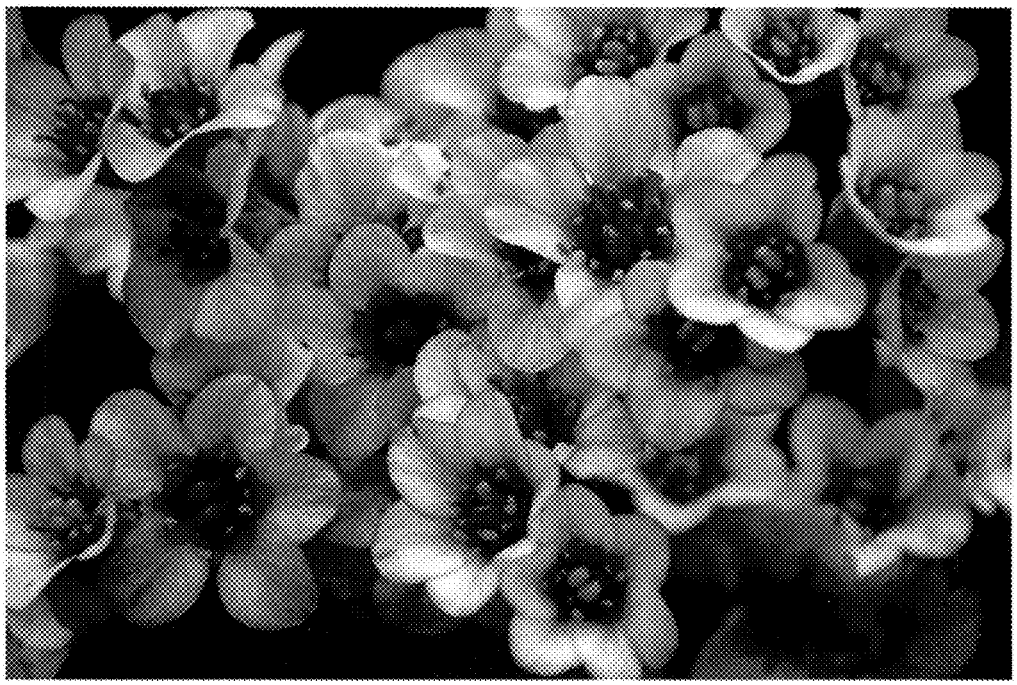
FIG. 2 shows a close-up of the young and mature flowers of the new plant in a partially-shaded greenhouse.

The following description is based on two-year-old plants growing in a partially-shaded greenhouse and in an outdoor full-sun display garden in Zeeland, MI, USA. Except for ordinary dictionary color usage, color references are according to The Royal Horticultural Society Colour Chart, 2015 edition. The new plant has not been observed in all possible growing conditions and may vary in phenotypic characteristics based on water availability, light conditions, fertilizer, temperatures, etc. without varying in genotypic characteristics.

Parentage: Female or seed parent 'Sakura'; male or pollen parent 12-1-6;

Asexual propagation: Division of tissue culture plants, about 21 days to initiate roots; time to finish 25 mm plugs in a one-gallon container about 3 months; moderate growth rate;

Plant habit: Low, spreading, herbaceous, evergreen, winter-hardy, perennial mound; with heavily branched flower stems; with about 6 to 8 shoots per plant; shoots to about 10 cm long and about 3.5 cm diameter;

Plant size: Foliage about 69 to 78 cm wide and about 38 cm tall; flowering to about 75 cm wide and about 54 cm tall;

Leaves: Alternate; simple; coriaceous; obovate; adaxial and abaxial surface lustrous; rounded apex; cuneate base; margin ciliolate and irregularly dentate to crenate; to 33 cm long and 27.5 cm wide, average about 27 cm long and about 22 cm wide;

Leaf color: Young expanding leaves adaxial nearest blend of RHS 137B and RHS 146A and abaxial nearest RHS 146C; mature leaves adaxial between RHS NN137Aand RHS 139A, mature abaxial between RHS 146A and RHS 139A; winter color developing variable, moderate to strong blush to solid nearest RHS 187A adaxial and nearest RHS 187B abaxial;

Veins: Pinnate;

Vein color: Young adaxial between RHS 137B and RHS 146A, abaxial between RHS 146D and RHS N144D; adaxial nearest RHS 137A, abaxial basally nearest blend between RHS 146D and RHS 145A;

Inflorescence: Panicle; about 6 to 8 per plant; to about 54 cm long and 2 cm diameter at base, flowering portion to about 25 cm tall and 22 cm wide; cylindrical; lustrous; glabrous;

Peduncle color: Variable, proximal portion nearest blend of RHS 145C and RHS 146D, distally nearest RHS 146D with minor to blushing to nearly solid of nearest RHS 178B;

Flower: Single; perfect; campanulate; on terminal branches; about 28 mm across, about 20 mm long; attitude outright to slightly drooping;

Flower fragrance: None detected;

Calyx: Campanulate; to about 13 mm wide and 10 mm long, forming hypanthium 3 mm long and 7 mm diameter;

Sepals: Typically, five, rarely six; ovate; broadly acute apex; truncate base fused in basal 6 mm; margin entire; glabrous and lustrous adaxial, lustrous and sparsely glandular abaxial; about 13 mm long and about 6 mm wide;

Sepal color: Variable; adaxial nearest RHS 146C with strong to moderate blush of nearest RHS 179B; abaxial nearest RHS 146C in the longitudinal center, with margins of nearest RHS 179B, and base nearest RHS 180D;

Flowering period: Beginning early spring, for about 4 weeks; producing up to 27 flowers per branch and up to 170 flowers per panicle;

Individual flower longevity: 7 to 10 days;

Flower buds one day prior to opening: Oblong, acute apex, about 15 mm long and 7 mm diameter;

Flower bud color one day prior to opening: Exposed petals nearest RHS NN155D, sepal base nearest RHS 179B with the distal one-half between RHS 174D and RHS 194A;

Pedicel: Cylindrical; glaucous; lustrous; to about 15 mm long and 2 mm diameter;

Pedicel color: Variable; nearest RHS 146C with a blush of nearest RHS 179B to between RHS 180B and RHS 179B;

Petals: Typically, five in a single whorl, rarely six; obovate; rounded apex; attenuate to cuneate base; margin entire; glabrous adaxial abaxial; imbricate near longitudinal middle; to about 21 mm long and 15 mm wide near middle; base tapering to about 2 mm across;

Petal color: Variable; when initially open adaxial and abaxial nearest RHS NN155D developing strong adaxial blush between RHS N57C to RHS 61C concentrated near longitudinal center with a thin margin, to marginal blush of nearest RHS 64B;

Androecium: Typically, ten, rarely twelve; about 12 mm long;

*Filament.*—Cylindrical; lustrous; glabrous; to about 11 mm long and 1 mm diameter; color initially translucent to nearest RHS NN155A, maturing to nearest RHS 180B distally and RHS NN155A proximally.

*Anther.*—Ellipsoidal; basifixed; longitudinal; about 2 mm long and 1 mm across; color nearest RHS 161A.

*Pollen.*—Abundant; color nearest RHS 18B.

Gynoecium: Bifid to rarely trifid; about 14 mm long, fused in basal 3 mm;

*Ovary.*—Partly inferior; 6 mm across at base and 3 mm tall; color initially nearest RHS 145C maturing to nearest RHS 145B.

*Style.*—Cylindrical; about 8 mm long and 4.5 mm diameter above ovary; color initially nearest RHS 145C maturing to nearest 146D with distal portion nearest RHS 60A.

*Stigma.*—Loosely lobed; about 4 mm wide and 2 mm tall; color initially nearest RHS N144C, at flower maturity between RHS 183C and RHS 183B.

Seed: Ellipsoidal; acute apex and rounded base; surface glabrous; about 2 mm long and 0.5 mm across center; color nearest RHS 200B;

Growth: *Bergenia* 'Peppermint Patty' is tolerant of winter temperatures from USDA hardiness at least from zones 4 to 8. The new plant grows best with good drainage and adequate moisture.

Pests and diseases: The new plant is not known to be more or less susceptible or tolerant of diseases and pests that are common to other Heartleaf *Bergenia* cultivars.

I claim:

1. A new and distinct cultivar of *Bergenia* plant named 'Peppermint Patty' as described and illustrated.

* * * * *